(12) United States Patent
Murray et al.

(10) Patent No.: US 12,270,808 B2
(45) Date of Patent: Apr. 8, 2025

(54) PARAMAGNETIC IMMUNOBEADS FOR THE ISOLATION OF HUMAN ADIPOSE-DERIVED STEM CELLS

(71) Applicant: University of Florida Research Foundation, Inc., Gainesville, FL (US)

(72) Inventors: John D. Murray, Jacksonville, FL (US); Edward W. Scott, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 1036 days.

(21) Appl. No.: 17/056,889

(22) PCT Filed: May 21, 2019

(86) PCT No.: PCT/US2019/033208
§ 371 (c)(1),
(2) Date: Nov. 19, 2020

(87) PCT Pub. No.: WO2019/226588
PCT Pub. Date: Nov. 28, 2019

(65) Prior Publication Data
US 2021/0208137 A1  Jul. 8, 2021

Related U.S. Application Data

(60) Provisional application No. 62/675,298, filed on May 23, 2018.

(51) Int. Cl.
| | | |
|---|---|---|
| *G01N 33/543* | (2006.01) | |
| *B03C 1/01* | (2006.01) | |
| *B03C 1/28* | (2006.01) | |

(52) U.S. Cl.
CPC ......... *G01N 33/54326* (2013.01); *B03C 1/01* (2013.01); *B03C 1/28* (2013.01); *B03C 2201/18* (2013.01); *B03C 2201/26* (2013.01)

(58) Field of Classification Search
None
See application file for complete search history.

(56) References Cited

U.S. PATENT DOCUMENTS

| | | | |
|---|---|---|---|
| 2002/0182751 A1 | 12/2002 | Herr et al. | |
| 2004/0142384 A1* | 7/2004 | Cohen | B03C 1/0335 435/7.2 |
| 2009/0304654 A1 | 12/2009 | Lue et al. | |
| 2010/0184220 A1* | 7/2010 | Ram-Liebig | A61L 27/3808 435/395 |
| 2010/0261274 A1* | 10/2010 | Vodyanyk | C12N 5/0647 435/363 |
| 2012/0149021 A1 | 6/2012 | Yung et al. | |
| 2014/0369973 A1* | 12/2014 | Bernstein | C12N 5/0647 435/372 |
| 2019/0175755 A1* | 6/2019 | Kosmides | A61K 39/395 |
| 2020/0077644 A1* | 3/2020 | Church | A01N 1/02 |

FOREIGN PATENT DOCUMENTS

| | | | | |
|---|---|---|---|---|
| WO | WO2013121216 A1 * | 8/2013 | | G01N 33/50 |

OTHER PUBLICATIONS

Zhu et al., Manual isolation of adipose-derived stem cells from human lipoaspirates, Journal of Visualized Experiments, Sep. 2013, 79, pp. 1-10. (Year: 2013).*
Silva et al., Magnetic targeting as a strategy to enhance therapeutic effects of mesenchymal stromal cells, Stem Cell & Therapy, 2017, 8:58, pp. 1-8. (Year: 2017).*
Balmayor et al.,Synthesis and functionalization of superparamagnetic poly-e-caprolactone microparticles for the selective isolation of subpopulations of human adipose-derived stem cells, J.R.Soc. Interface, 20118, pp. 896-908. (Year: 2011).*
Francis et al., Isolating adipose-derived mesenchymal stem cells from lipoaspirate blood and saline fraction, Organogenesis, 6:1 2010, pp. 11-14. (Year: 2010).*
International Search Report issued for PCT/US2019/033208, mailed Aug. 6, 2019.
Bryan et al., Evaluation of a Novel Non-Destructive Catch and Release Technology for Harvesting Autologous Adult Stem Cells, PLOS One, vol. 8(1):e53933, p. 1-8m 2013.
Ratajczak et al., CD133 Expression Strongly Correlates with the Phenotype of Very Small Embryonic/Epiblast-like Stem Cells, Adv. Exp Med Biol., vol. 777, p. 125-41, 2013.
Hamid et al., Characterization of human adipose-derived stem cells and expression of chondrogenic genes during induction of cartilage differentiation, Clinics (Sao Paulo), vol. 67(2), p. 99-106, 2012.

* cited by examiner

*Primary Examiner* — Gary Counts
(74) *Attorney, Agent, or Firm* — Thomas|Horstemeyer, LLP

(57) ABSTRACT

Disclosed herein are compositions, devices, and methods for isolating human Adipose-derived stem cells (ASCs) without either electricity or enzymatic digestion. In particular, a paramagnetic immunobead (PIB) for isolating human ASCs is disclosed. In some embodiments, the PIB displays on its surface one or more antibodies that selectively bind ASC-specific antigens. Also disclosed is a method for isolating human ASCs using the disclosed PIBs.

5 Claims, 8 Drawing Sheets

PARAMAGNETIC IMMUNOBEADS FOR THE ISOLATION OF HUMAN ADIPOSE-DERIVED STEM CELLS

CROSS-REFERENCE TO RELATED APPLICATIONS

This application is a National Stage of International Application No. PCT/US2019/033208, filed May 21, 2019, which claims benefit of U.S. Provisional Application No. 62/675,298, filed May 23, 2018, which is hereby incorporated herein by reference in its entirety.

BACKGROUND

Adipose-derived stem cells (ASCs) have shown promise in both cell-based therapies as well as in tissue regeneration. Such promise is anchored in the fact that these cells differentiate along mesodermal lineages, with the ability to repair or replace tissues such as in the heart, skeletal system, nerves, and muscles. Several mechanical and enzymatic techniques have been developed to isolate the stromal vascular fraction (SVF), which contains the ASC population, from lipoaspirate. While these techniques prove effective, they also require electricity to power instrumentation to process the lipoaspirate (such as to power centrifuges or to produce suction for cell isolation). However, with over 1 billion people living without access to electricity worldwide, delivering stem cell-based regenerative therapies to this population would be extremely difficult if not impossible. Moreover, many of these methods rely on enzymes such as collagenase, trypsin or dispase, which are costly and can impact on safety and efficacy.

SUMMARY

Disclosed herein are compositions, devices, and methods for isolating human ASCs without either electricity or enzymatic digestion. In particular, a paramagnetic immunobead (PIB) for isolating human ASCs is disclosed. In some embodiments, the PIB displays on its surface one or more antibodies that selectively bind ASC-specific antigens. Therefore, in some embodiments, the PIB can comprise a magnetic material displaying on its surface a first antibody that selectively binds human CD90, a second antibody that selectively binds human CD44, a third antibody that selectively binds human CD105, a fourth antibody that selectively binds human CD73, or any combination thereof. Therefore, in some embodiments, the PIB displays on its surface the following antibody combinations: anti-CD90, anti-CD44, anti-CD105, and anti-CD73; anti-CD90, anti-CD44, and anti-CD105; anti-CD44, anti-CD105, and anti-CD73; anti-CD90, anti-CD105, and anti-CD73; anti-CD90, anti-CD44, and anti-CD73; anti-CD90 and anti-CD44; anti-CD90 and anti-CD105; anti-CD90 and anti-CD73; anti-CD44 and anti-CD105; anti-CD44 and anti-CD73; or CD105 and anti-CD73. In some embodiments, the FIB displays on its surface a first antibody that selectively binds human CD90, a second antibody that selectively binds human CD44, a third antibody that selectively binds human CD105, and a fourth antibody that selectively binds human CD73. In some of the above embodiments, the FIB further displays on its surface an antibody that selectively binds another antigen expressed by the stromal vascular fraction (SVF) of a lipoaspirate.

In some embodiments, the magnetic material is a paramagnetic spherical polymer particle, such as Bangs Laboratories' Estapor® Encapsulated microspheres, DYNAL's Dynabeads, Miltenyi microbeads or nanobeads, or Spherotech's smooth surface magnetic particles.

Methods for functionalizing magnetic materials with antibodies are known in the art. In some cases, a primary antibody is first conjugated to the surface of the magnetic surface. In these embodiments, the primary antibody selectively binds a constant region of the first antibody, second antibody, third antibody, fourth antibody, and any combination thereof.

Also disclosed is a method for isolating human adipose-tissue derived stem cells (ASCs). Adipose/fat tissue provides an abundant source of stromal vascular fraction (SVF) cells, and can also give rise to a substantial number of cultured, multipotent adipose-derived stromal cells (ADSCs), The disclosed method involves obtain a lipoaspirate from a human subject and mixing the lipoaspirate with the disclosed PIBs under conditions suitable to allow binding of the PIBs to SVF cells in the lipoaspirate expressing CD90, CD44, CD105, and CD73. A magnetic field can then be applied to the lipoaspirate to immunoprecipitate a stromal vascular fraction (SVF). Centrifugation can also be used, instead of or in addition to the magnetic field, to produce the immunoprecipitate. Once the lipoaspirate is discarded, the immunoprecipitate can be resuspended, and the SVF fraction can be cultured under conditions suitable to expand ASCs from the SVF.

Suitable methods for generating a magnetic field are known in the art. For example, the magnetic field can be applied using a neodymium magnet.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 8A shows chondroblast differentiation: gross chondrosphere (arrow) with representative indirect micrograph illustrating a sulfated proteoglycan sphere (inset) stained with Alcian Blue & Nuclear Fast Red, consistent for chondroblasts. Sphere diameter about 3 mm. FIG. 8B shows osteoblast differentiation: phase contrast 20× micrograph illustrating alkaline phosphatase staining with Alizarin Red, consistent for osteoblasts. FIG. 8C shows adipocyte differentiation: phase contrast 10× micrograph illustrating large lipid filled droplets, consistent for adipocytes (higher power inset with lipid droplet staining by Oil-Red-O).

DETAILED DESCRIPTION

Figure 1:
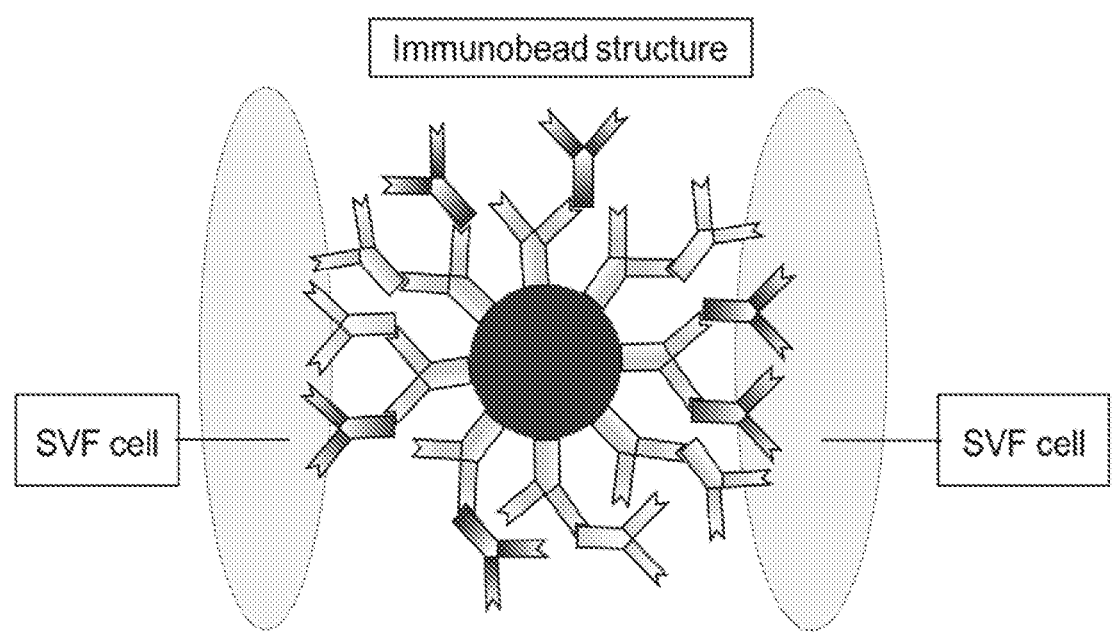
FIG. 1 is a schematic of a programmed paramagnetic immunobead structure. Primary and secondary IgG antibodies are built onto a paramagnetic Dynabead® to reduce possible steric hindrance of SVF cellular conjugation. Secondary antibodies conjugate to adipose-derived stem cells, such as mouse anti-human antibodies against CD90, CD44, CD105, and CD73, are labeled with fluorochromes, such as FITC, PE, Percp cy5.5, and APC.

Disclosed herein is a technique for the isolation of SVF from lipoaspirate using PIBs with a head-to-head comparison to isolation of SVF with a highly purified collagenase. For enzymatic SVF isolation, 15 mls of concentrated lipoaspirate underwent digestion with Corase® (a highly purified GMP collagenase, Reviticell, Inc., Jacksonville, FL) and subsequent centrifugation for a resultant SVF pellet. For immunobead SVF isolation, paramagnetic beads (Dynabeads® Protein G Kit, Thermo Fisher Scientific, Waltham, MA, cat #10007D) initially underwent antibody binding using rabbit anti-mouse IgG (H+L) Superclonal™ Antibody (Thermo Fisher Scientific, Cat #A27022). Secondary mouse anti-human antibodies to include CD90, PE CD44, CD105, and CD73 (Human MSC Analysis Kit, BD Biosciences, cat #562245) were then conjugated to the primary antibody to construct the PIBs. The PIBs were then added to 15 mls of lipoaspirate in a 15 mL coned tube and the tube was manually held and rotated for 10 minutes. A neodymium magnet (3×0.2×0.5 inch, part #M3055-002B2, Amazon.com) was then placed adjacent to the tube. Over a 10 minute period, the beads with their conjugated SVF were pulled from the lipoaspirate and the lipoaspirate was discarded. The SVF from both isolation techniques then underwent automated trypan blue cell counting (Countess™ II, Thermo Fisher Scientific, cat #AMQAX1000) and culturing with mesenchymal stem cell defining media (cat #05449, STEMCELL Technologies, Vancouver, BC). At culture day 14, the cells were analyzed for plastic adherence and morphology. Live cell count per mL lipoaspirate processed was $7.7 \times 10^4$ for isolation using collagenase and $9.6 \times 10^4$ for isolation using PIBs. Both sets of cells underwent plastic adherence and similar colony formation and morphology in culture, diagnostic of selection for adipose-derived stem cells. This study confirms the proof of concept that PIBs isolate SVF from lipoaspirate and possibly with greater efficacy comparative to collagenase methods. Isolation of SVF with PIBs is rapid and uses only handheld instrumentation without the use of electrical power. Such technology may be particularly useful for regenerative therapies in developing countries, where over 1 billion people may now receive novel stem cell therapies.

Definitions

"Adipose-derived stem cells," "adipose tissue-derived stem cells," and ASC (or ASCs) are used interchangeably herein and refers to multipotent stromal cells or stem cells that originate from adipose tissue and are capable of self-renewal. The adipose tissue may be brown or white adipose tissue, derived from subcutaneous, omental/visceral, mammary, gonadal, or other adipose tissue site. Preferably, the adipose is subcutaneous white adipose tissue. The adipose tissue may be from a human subject. Adipose tissue can autologous or allogeneic. These cells express a unique combination of cell surface proteins that can include, but are not limited to, stem cell marker CD34 and CD90, the tetraspan protein CD9, CALLA (CD10), aminopeptidase N (CD13), integrin 1 (CD29), hyaluronate receptor (CD44), integrin .alpha. 4 and 5 (CD49d, CD49e), ICAM-1 (CD54), decay accelerating factor (CD55), complement protectin (CD59), endoglin (CD105), VCAM-1 (CD106), Muc-1,8 (CD146), and ALCAM (CD166).

A number of embodiments of the invention have been described. Nevertheless, it will be understood that various modifications may be made without departing from the spirit and scope of the invention. Accordingly, other embodiments are within the scope of the following claims.

EXAMPLES

Example 1: Paramagnetic Immunobead Isolation of Human Adipose-Derived Stem Cells The purpose of this study is to quantitate the nucleated cells of the SVF isolated using PIBs. A head-to-head comparison will be made to the simultaneous isolation of SVF using a proteolytic enzyme, a GMP highly purified collagenase. After initial counting, the respective SVF populations will then be cultured within mesenchymal stem cell-defining media for identification of ASCs, as a measure of functional quality.

Methods

SVF Isolation by Enzymatic Digestion

Using the "Reviticell Kit" (Reviticell, Inc., Jacksonville, FL) with its inherent 10-step process, beginning with 70 mls of unconcentrated lipoaspirate, 17.5 ml of lipoaspirate was placed into each of four 35 ml custom Transfer Syringes (produced for Reviticell by Cardinal Health, Dublin, OH). Subsequently, 20 ml of normal saline was added to each syringe and a homogenous suspension was created. The plunger rods were then removed and the four Transfer Syringes were centrifuged for 3 minutes at 340×g (Drucker Diagnostics, 755VES, State College, PA). The concentrated pellet at the bottom of each of the four Transfer Syringes was then added to a Concentrate Syringe (standard 35 ml syringe). After discarding the aqueous infranatant from two of the Transfer Syringes, 7.5 ml of lipoaspirate lowest in the adipose column of each of the two Transfer Syringes was transferred to the Concentrate Syringe. A Corase® Syringe (standard 35 ml syringe pre-labeled as such by Reviticell) then received 10 ml of phosphate buffered saline and Corase®.

Aliquots of Corase® (0.5 ml sterile water with 1 mg of Corase® were prepared preoperatively). Corase® is identical to Liberase MNP-S, which is a blended collagenase meeting current Good Manufacturing Practice guidelines. It is a purified (not crude) blend of three enzymes: collagenase I, collagenase II, and thermolysis. Corase® specific activity is 3.8 U/mg, or activity of 19-32 Wunsch Units.

The contents of the Concentrate Syringe were then transferred to the Corase® Syringe (thus containing 15 mls of concentrated lipoaspirate with centrifuged pellets from all four centrifuged Transfer Syringes). The Corase® Syringe was then placed into an incubating rocking platform shaker (VWR, Radnor, PA) at 370 C for 20 minutes at tilt level of 6 and speed of 30. Half of the contents of the Corase® Syringe was then transferred to each of two Transfer Syringes. To these syringes, 20 ml of saline was added and subsequently centrifuged for 3 minutes. After removal of the supernatant, the resultant pellet, also defined as the SVF, was resuspended in 1 mL of Dulbecco's phosphate buffered saline (STEMCELL Technologies, cat #37350) for subsequent cell counting and culture.

SVF Isolation by PIB Immunoprecipitation

Using the Dynabeads® protein Using the Dynabeads® protein G immunoprecipitation kit (Thermo Fisher Scientific, Waltham, MA, cat #10007D), the Dynabeads® were resuspended by vortex for 30 seconds. Then, 50 µL of Dynabeads® were added to a microfuge tube. A neodymium magnet (3×0.2×0.5 inch, part #OM3055-002B2, Amazon.com), the only magnet used in this experiment, was then placed next to the tube to precipitate the beads and the supernatant was removed. Then, 200 µL of antibody binding and washing buffer (in the kit) was added. Then, 5 µL of rabbit anti-mouse IgG antibody (Thermo Fisher Scientific, cat #A27022) was added to the beads in suspension. The suspension was then rotated (360° rotation, HulaMixer®, Thermo Fisher Scientific, cat #15920D) for 10 minutes at room temperature. The beads were then precipitated once again with the magnet and the supernatant was removed and 200 µL of the washing buffer was added. Then, 5 µL each of mouse anti-human IgG antibody of CD90, CD44, CD105, and CD73 was added to the tube and incubated in similar rotation for 10 minutes. The supernatant was removed after magnetic precipitation and 200 µL of the washing buffer was added and the programmed paramagnetic beads, now PIBs, were then briefly vortexed to homogeneous suspension (FIG. 1).

Figures 2A, 2B, 2C:
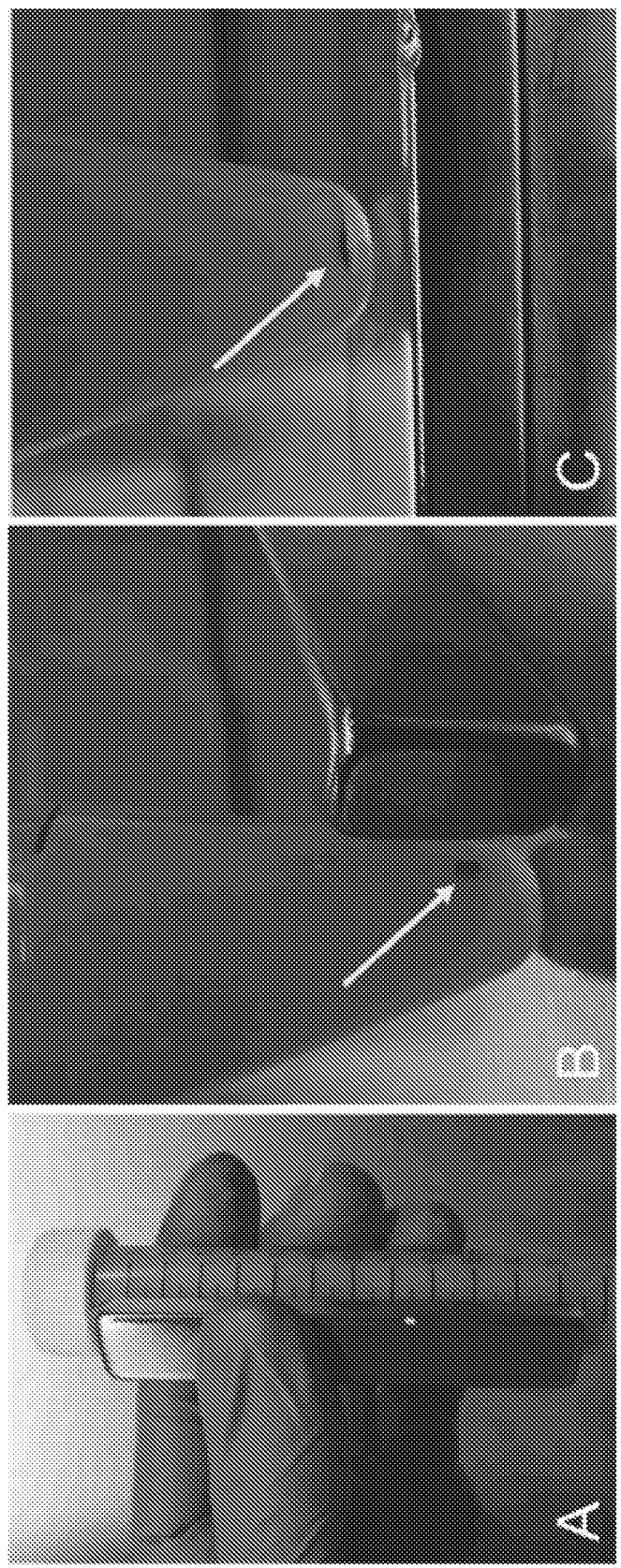
FIGS. 2A to 2C show a sequence of magnetic precipitation of paramagnetic immunobeads (PIBs) and conjugated cells. The neodymium magnet is moved from alongside an upright 15 mL coned tube (holding the homogeneous lipoaspirate-PIB suspension) to the bottom of the coned end of the tube (FIGS. 2A-2C) to precipitate the PIB-SVF fraction over a 10-minute period. The arrows denote the Dynabeads®. The lipoaspirate is then simply discarded.

Beginning with 30 mL of unconcentrated lipoaspirate in a 60 mL syringe, the syringe was placed to a plunger upright position. After approximately 15 minutes, the aqueous infranatant was discarded from the syringe, leaving a homogeneous lipoaspirate suspension. 15 mls of the lipoaspirate suspension was then added to an empty 15 mL polypropylene coned tube and the 200 µL suspension of PIBs was added to the tube. The tube was capped and then held and rotated in hand for 10 minutes. With the tube returned to upright position, the magnet was then placed adjacent to the long axis of the tube. Over 10 minutes, the magnet was then steadily moved toward the coned bottom of the tube to ultimately precipitate the PIBs and attached SVF at the bottom of the cone (FIGS. 2A-2C). The lipoaspirate was then discarded and the PIBs were resuspended in 1 mL of Dulbecco's phosphate buffered saline (STEMCELL Technologies, cat #37350) for subsequent cell counting and culture. No attempt to unconjugate the PIBs from the SVF was made.

Cell Counting and Viability Testing

10 µL samples from the SVF of the enzyme and FIB suspensions then underwent automated cell counting and trypan blue viability testing in accordance to the manufacturer's instructions (Countess™ II, Thermo Fisher Scientific, cat #AMQAX1000). Final count was the average of two counts respectively.

ASC Expansion

The SVF from each of the two suspensions was added to 5 mls of animal component free defined media (MesenCult-ACF basal medium #05451 and 5× supplement #05452, STEMCELL Technologies, Vancouver, BC) into a T-25 culture flask (pre-treated with attachment substrate, STEMCELL Technologies, #05444. Flask: VWR, Nunclon tissue culture flask #470174-450) and incubated at humidified 5% carbon dioxide. Half media change was performed at day 6 with complete media change at day 10). Observation of ASC adherence and morphology was completed and recorded on culture day 14.

Results

Figure 3:
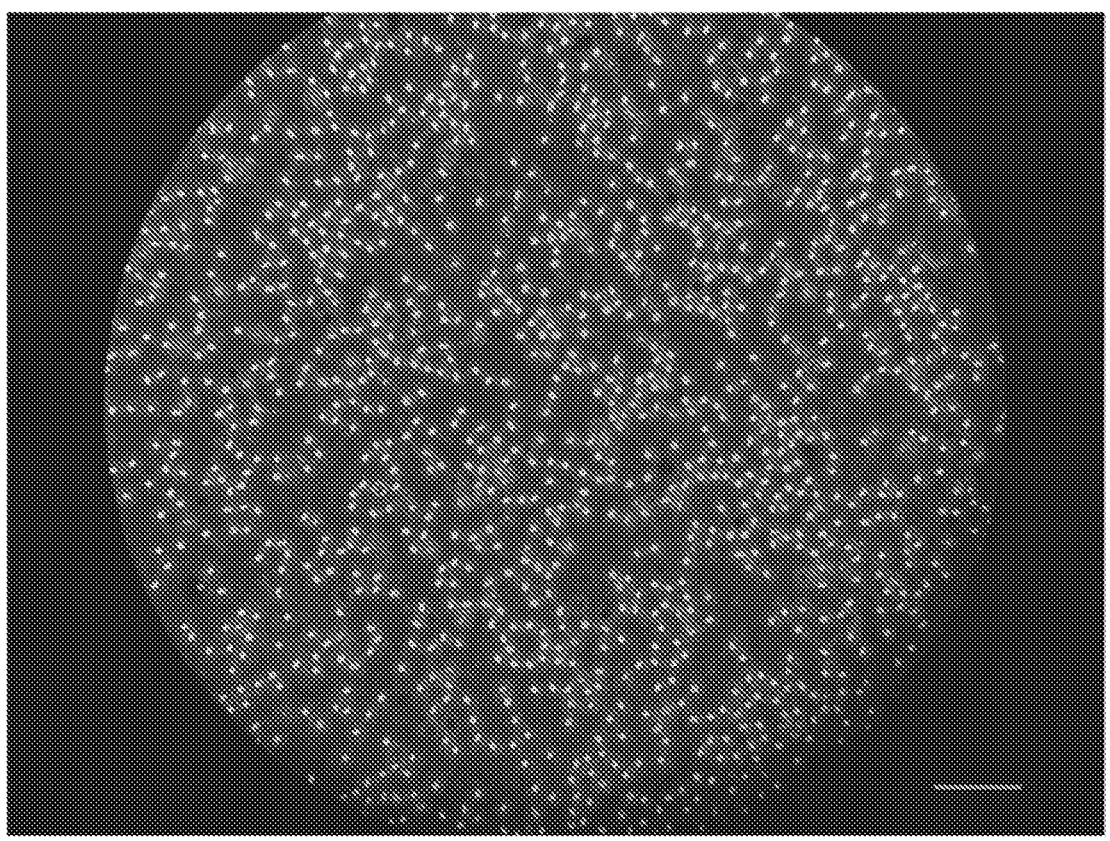
FIG. 3 is a bright-field micrograph of PIB-isolated SVF with trypan blue. Though best seen in real-time microscopy, the live cells (are studded with PIBs, (40×, measurement bar 50 μm).

FIG. 3 is a bright-field micrograph of PIB-isolated SVF with trypan blue. Though best seen in real-time microscopy, the live cells (light colored) are studded with PIBs. (40×, measurement bar 50 µm).

Figure 4A:
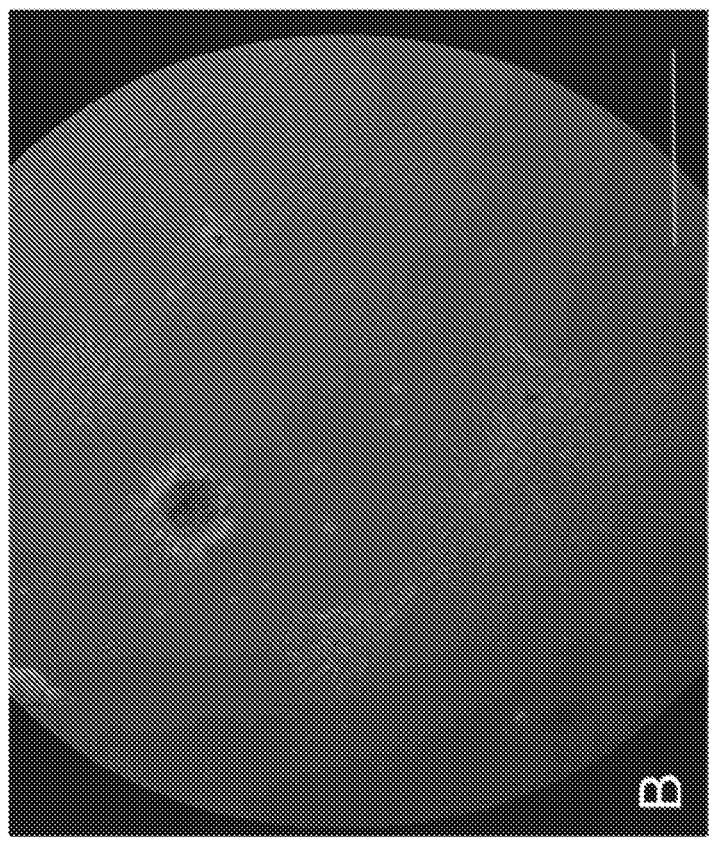
FIGS. 4A and 4B are bright-field micrographs of culture morphology (day 14) of PIB-isolated SVF (FIG. 4A) and collagenase-isolated SVF (FIG. 4B). Both cultures display colony formation and typical branching patterns of adipose-derived stem cells (ASCs). The PIB-isolated ASCs display comparatively larger and more densely developed spheroids than the collagenase-isolated ASCs. While many of the PIBs remain conjugated to the ASCs, the rest have become spontaneously unconjugated and free floating. (10×, measurement bar is 0.5 mm).
Figure 4B:
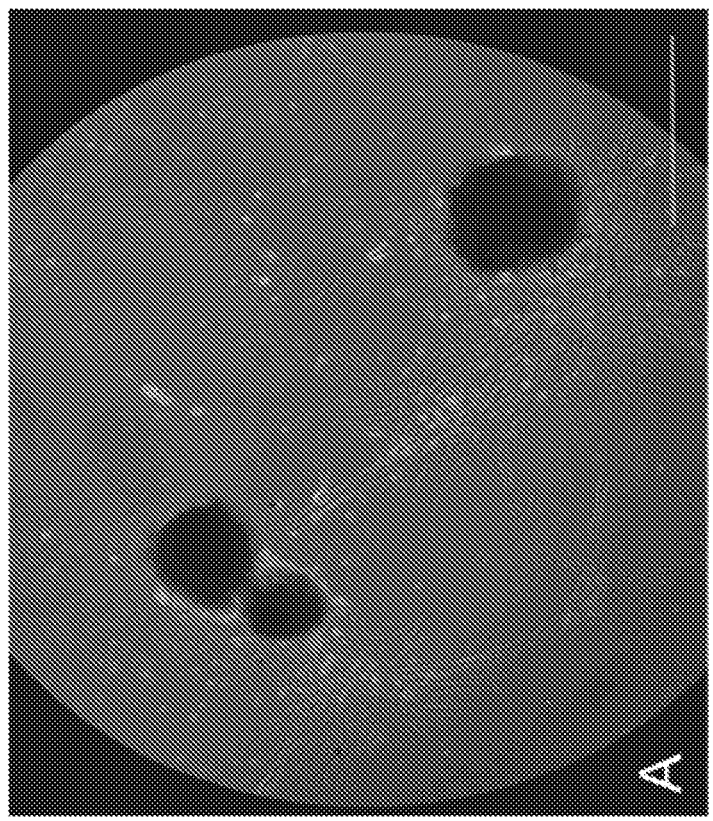

FIGS. 4A and 4B are bright-field micrographs of culture morphology (day 14) of RIB-isolated SVF (FIG. 4A) and collagenase-isolated SVF (FIG. 4B). Both cultures display colony formation and typical branching patterns of adipose-derived stem cells (ASCs). The PIB-isolated ASCs display comparatively larger and more densely developed spheroids than the collagenase-isolated ASCs. While many of the PIBs remain conjugated to the ASCs, the rest have become spontaneously unconjugated and free floating. (10×, measurement bar is 0.5 mm).

Figure 5:
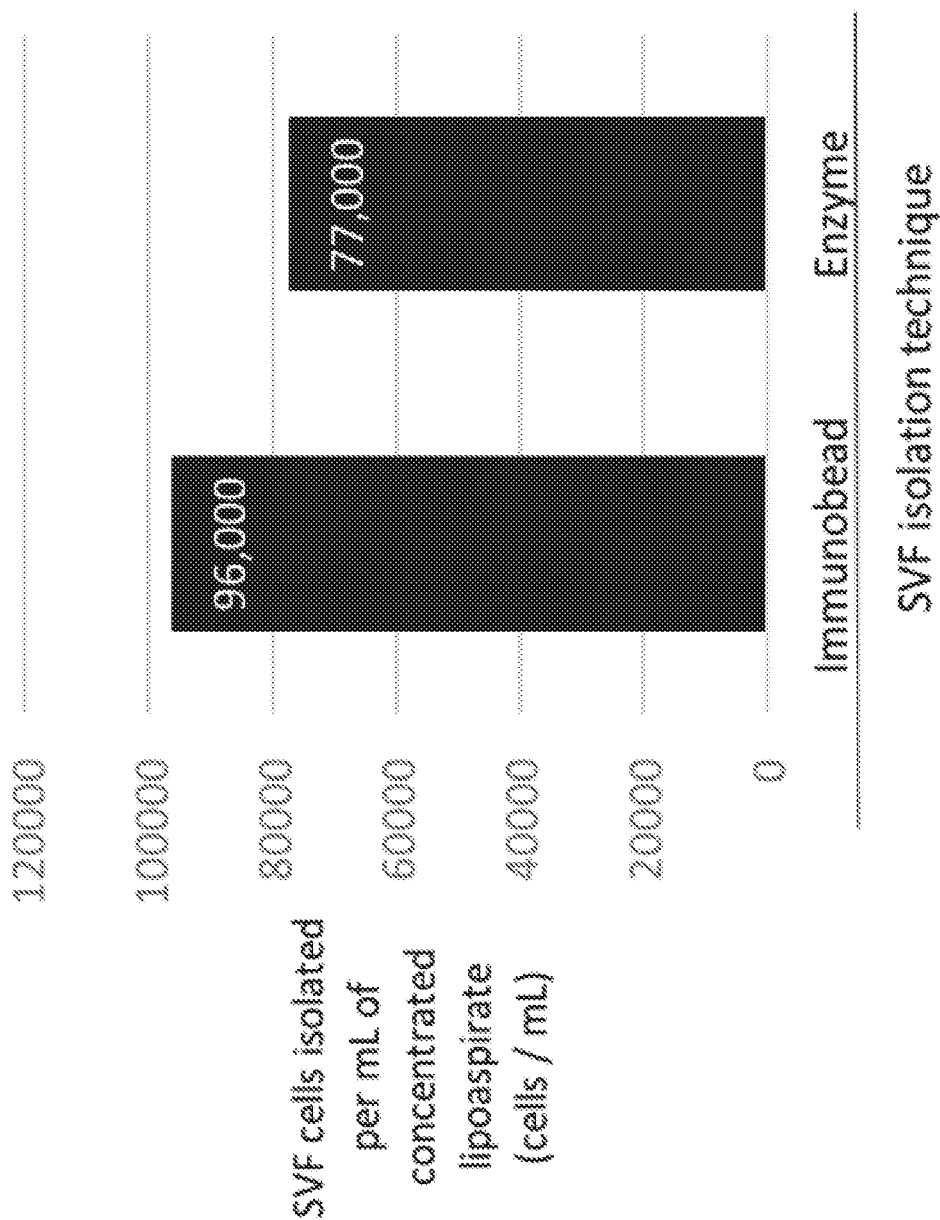
FIG. 5 is a bar graph showing cell counts of live nucleated cells of the stromal vascular fraction (SVF) isolated using paramagnetic immunobeads (PIBs) as well as SVF isolated using enzyme (GMP grade highly purified collagenase). 20% more cells were isolated using PIBs than enzyme.

FIG. 5 is a bar graph showing cell counts of live nucleated cells of the stromal vascular fraction (SVF) isolated using paramagnetic immunobeads (PIBs) as well as SVF isolated using enzyme (GMP grade highly purified collagenase). 20% more cells were isolated using PIBs than enzyme.

Conclusions

Rapid isolation of SVF from lipoaspirate is possible using antibody-coated paramagnetic beads (Dynabeads®) and a handheld neodymium magnet. Healthy ASCs grew from the PIB-SVF population and SVF cell counts and subsequent ASC culture morphologies were similar to the enzyme-SVF population. After the paramagnetic beads were programmed with the antibodies, no electrical power was needed for this SVF isolation.

Example 2

Methods

Lipoaspirate Harvest

Fresh human lipoaspirate obtained from informed and consented healthy females was used for this study. The lipoaspirate had been harvested using standard operative tumescent techniques using syringe liposuction. The tumescent solution included normal saline, lidocaine, and epinephrine. Shortly after harvest, the fresh lipoaspirate underwent 20 intersyringe transfers (10 mls syringes). After separating into principally aqueous and adipose layers, the aqueous layer was decanted. The remaining adipose layers were combined for a total working volume of 15 mls. This study incorporated triple biological replicates with double technical replicate testing for cell quantity (average taken) and electron microscopy.

ASC-Paramagnetic Immunobead (aPIB) Preparation aPIBs were prepared to recognize a panel of ASC cell surface markers (CD90, CD44, CD105, and CD73) using the Dynabeads® protein G immunoprecipitation kit (Thermo Fisher Scientific, Waltham, MA, cat #10007D) according to the manufacturer's instructions. Briefly, 50 µL of the Dynabeads® were conjugated to protein G in a microfuge tube. A neodymium magnet (3×0.2×0.5 inch, Omega Magnets, Carpinteria, CA) was then placed next to the tube to precipitate the beads and the supernatant was removed. To the bead suspension, 200 µL of antibody binding and washing buffer and 5 µL of rabbit anti-mouse IgG antibody (Thermo Fisher Scientific, cat #A27022) were added. The suspension was then rotated (360° rotation, HulaMixer®, Thermo Fisher Scientific, cat #15920D) for 10 minutes at room temperature. The beads were then precipitated once again with the magnet and the supernatant was removed and 200 µL of the washing buffer was added. Then, 5 µL each of mouse anti-human IgG antibodies of markers CD90, CD44, CD105, and CD73 (BD Biosciences, Franklin Lakes, NJ, cat #562245), suitable for ASC enrichment, were added to the tube and incubated in similar rotation for 10 minutes. The supernatant was removed after magnetic immunoprecipitation and 200 µL of the washing buffer was added and the programmed paramagnetic beads, now aPIBs, were then briefly vortexed to homogeneous suspension. A structural aPIB diagram is seen in FIG. 1.

aPIB Immunoprecipitation

The 15 mls of lipoaspirate was added to an empty 15 mL polypropylene coned tube and the 200 µL suspension of PIBs was added to the tube. The tube was capped and then held and rotated in hand for 10 minutes. With the tube returned to the upright position, the magnet was then placed parallel and adjacent to the long axis of the tube. Over the next 10 minutes, the magnet was steadily moved toward the coned bottom of the tube to precipitate the aPIBs to the bottom of the coned tube (see FIG. 2). The lipoaspirate was then discarded and the aPIBs were resuspended in 1 mL of Dulbecco's phosphate buffered saline (STEMCELL Technologies, cat #37350) for subsequent cell counting and culture. No attempt to unconjugate the PIBs from the ASCs was made.

aPIB Cell Counting

10 µL samples from the aPIB suspension then underwent automated cell counting and trypan blue viability testing in accordance with the manufacturer's instructions (Countess™ II, Thermo Fisher Scientific, cat #AMQAX1000). Final count was the average of two counts respectively.

aPIB Morphologic Evaluation aPIBs underwent morphologic evaluation using scanning electron microscopy (SEM). aPIB suspensions were gently filtered onto poly-L-lysine treated 0.2 um Millipore filters and fixed with 2.5% glutaraldehyde, 4% paraformaldehyde in 1×PBS, pH 7.24. Filters with aPIBs were washed with 1×PBS followed by deionized water and dehydrated in a graded ethanol series (25%, 50%, 75%, 95%, and 100%). Dehydrated cells were then loaded into the critical point dryer with bone dry CO2 (Autosamdri-815, Tousimis, Rockville, MD). Dried membrane filters containing aPIBs were mounted onto aluminum stubs with carbon adhesive tabs, sputter coated with Au/Pd (DeskV, Denton, Moorestown, NJ) and imaged with Hitachi SU5000 FE-SEM (Hitachi High Technologies, Schaumburg, IL).

aPIB Immunophenotyping

Samples of the aPIB suspension were run on a BD LSR II (BD Biosciences, San Jose, CA) flow cytometer with accompanying analytical software (BD FACSDiva™). The aPIBs were suspended in BD Pharmingen™ Stain Buffer (cat #554656). In accordance with the Becton-Dickenson Stemflow™ kit, 100 µl of the prepared suspension was added equally to all analysis tubes to include FITC mouse anti-human CD90, PE mouse anti-human CD44, PerCP-Cy™ 5.5 mouse anti-human CD105, and APC mouse anti-human CD73 with positive and negative controls and positive and negative cocktails. After the cell suspensions were added, the tubes were incubated in the dark for 30 minutes and the cells were then washed twice with BD Pharmingen™ Stain Buffer and resuspended to 500 µl in BD Pharmingen™ Stain Buffer. Cells were then kept in the dark and on ice until analysis later that same day.

ASC Expansion

The aPIBs were added to 5 mls of animal component free defined media (MesenCult-ACF basal medium #05451 and 5× supplement #05452, STEMCELL Technologies, Vancouver, BC) into a T-255 25 culture flask (pre-treated with attachment substrate, STEMCELL Technologies, #05444. Flask: VWR, Nunclon tissue culture flask #470174-450) and incubated at humidified 5% carbon dioxide. Half media change was performed at day 6 with complete media change at day 10. Observation of ASC adherence and morphology were completed and recorded around culture day 14.

Tri-Lineage Differentiation to Confirm ASC Enrichment

Expanded cells at initial 80% confluence (typically culture day 6 or 7) were dissociated from the culture flask (Mesencult-ACF Dissociation Kit #05426, Stemcell™ Technologies). ASCs were first passaged and seeded on six-well culture plates at approximately 100,000 cells per well. After attachment, cells were grown to approximately 80% confluence. Each well received a different respective differentiation medium.

For osteogenic differentiation, basal growth media was exchanged for conditioned osteogenic differentiation medium (Stemcell™ Technologies, Mesencult™ Osteogenic Stimulatory Kit #05404), Alizarin Red (Sigma-Aldrich, St. Louis, MO) staining was performed (to specifically stain alkaline phosphatase deposits) on day 14 and photomicrographs were obtained using whole field bright-light microscopy captured at 15×.

For adipogenic differentiation, basal growth media was exchanged for conditioned adipogenic differentiation medium (Stemcell™ Technologies, Mesencult™ Adipogenic Differentiation Medium #05412). Oil red O (Sigma-Aldrich) staining was performed (to specifically stain the lipid droplets) on day 14 and microphotographs were obtained using whole field bright-light microscopy captured at 15×.

For chondrogenic differentiation, basal growth media was exchanged for conditioned chondrogenic differentiation medium (Stemcell™ Technologies, Mesencult™ Chondrogenic Differentiation Medium #05455). Alcian Blue/Nuclear Fast Red (Sigma-Aldrich) staining was performed (to specifically stain sulfated proteoglycans) on day 14 and photomicrographs were obtained. The micromass chondrosphere was photographed by indirect microscopy.

Results aPIB Cell Counting

Live cell count per mL lipoaspirate processed was $9.6 \times 10^4$.

aPIB Morphologic Evaluation

Figure 6:
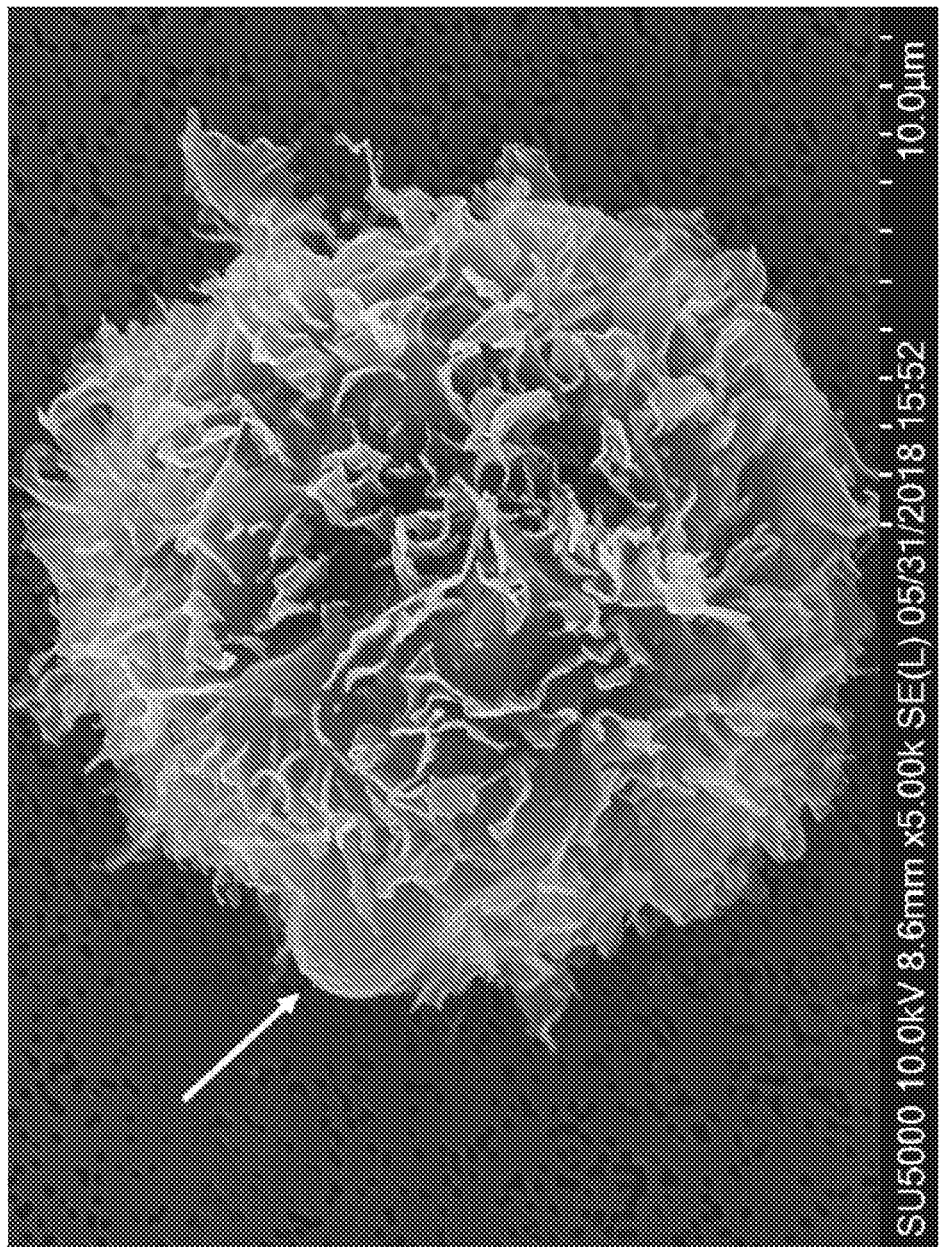
FIG. 6 is a scanning electron micrograph of a cell phenotypically consistent with an adipose-derived stem cell conjugated to a paramagnetic immunobead (arrow).

The initial goal was to ensure that the aPIB based ASC enrichment protocol was directly isolating cells with an ASC morphologic phenotype. Therefore, scanning electron microscopy (SEM) of the aPIB isolates (FIG. 6) was performed. While cells phenotypically consistent with erythrocytes and lymphocytes were seen, the PIBs were only attached to cells morphologically consistent with ASCs. This visually confirmed that the direct isolation protocol enriches for cells with the expected ASC phenotype, not random cell precipitation. It was suspect that processing of the samples for SEM unconjugated many of the PIBs from ASCs.

aPIB Immunophenotyping

Figure 7:
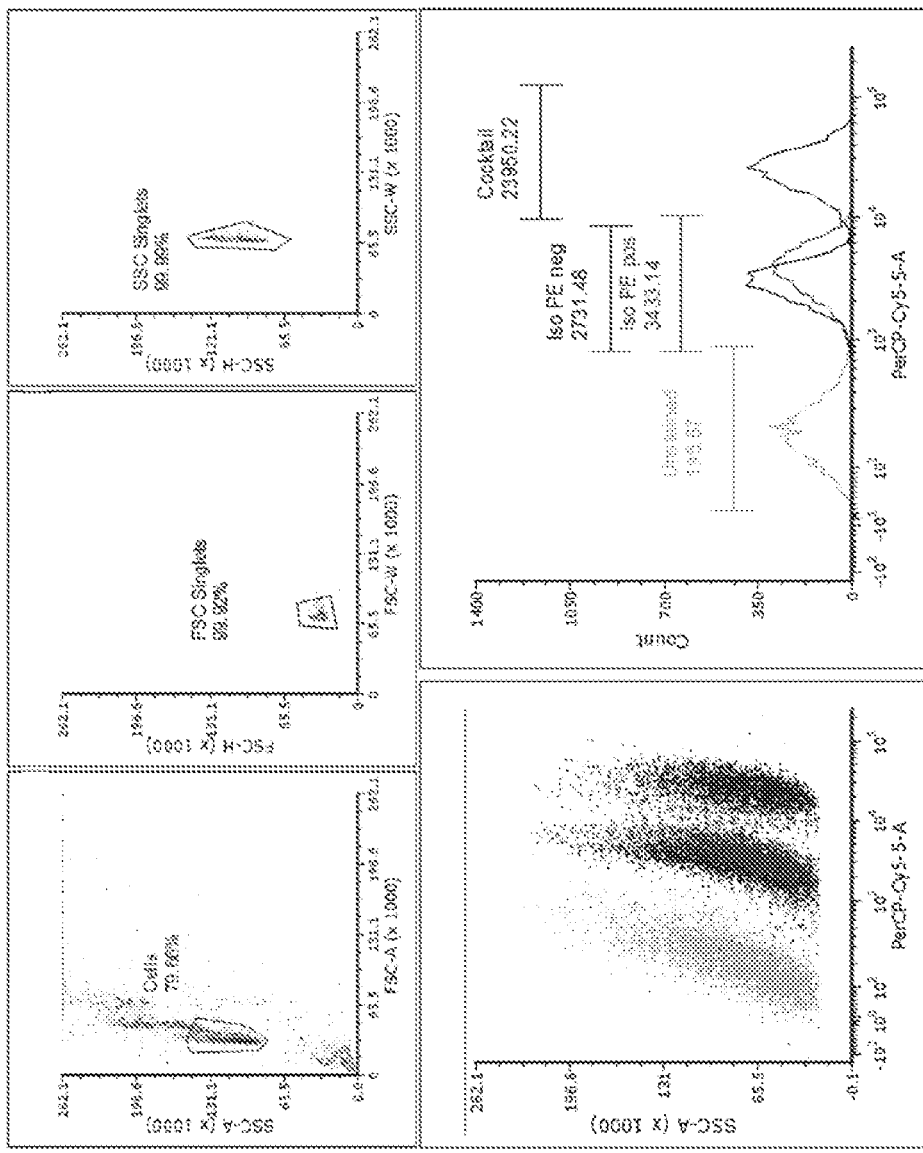
FIG. 7 shows immunophenotyping of primary adipose-derived cells isolated with paramagnetic immunobeads. Top row: scatterplot displaying respective gating to singlets. Bottom row: scatterplot (left) and histogram (right) clearly displaying positive CD105 ("cocktail" included PerCP-Cy™ 5.5-CD105). While FITC-CD90 also displayed similar positivity, APC-CD73 422 and PE-CD44 were not clearly appreciated due to the auto-fluorescence of the paramagnetic immunobeads.

Immunophenotyping by flow cytometry confirmed cells positive for markers CD90 and CD105 (FIG. 7). While the fluorochromes of FITC (CD90) and PerCP-Cy™ 5.5 (CD105) were clearly displayed, the auto-fluorescence of the Dynabeads® masked the fluorescence of APC (CD73) and PE (CD44). While the flow of the aPIB suspension through the aspiration nozzle did slow from time to time, dilution of the sample with stain buffer helped to re-establish faster flows.

ASC Functional Analysis by Differentiation

Figure 8C:
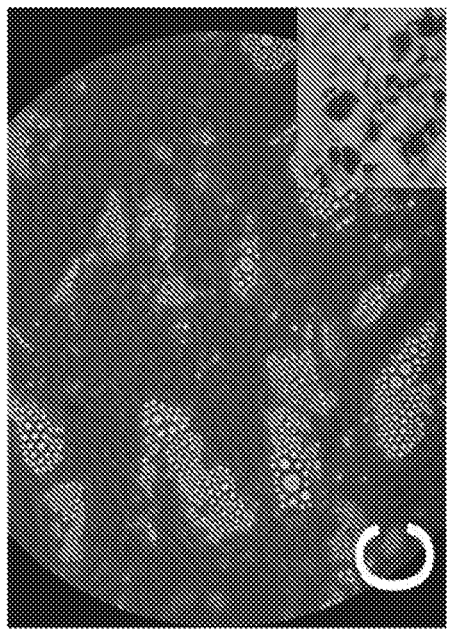
FIGS. 8A to 8C show tri-lineage differentiation of adipose-derived stem cells precipitated with paramagnetic immunobeads.
Figure 8B:
Figure 8A:
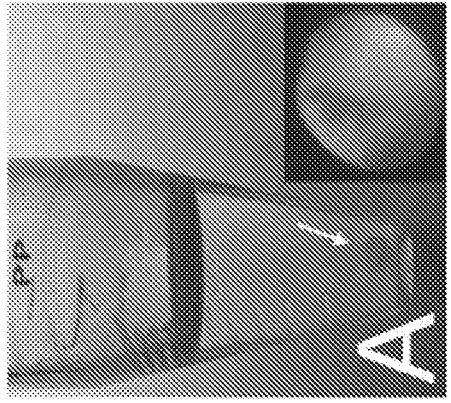

The ASCs underwent plastic adherence, colony formation, and sphere formation, 309 phenotypically diagnostic of adipose-derived stem cells (FIGS. 4A and 4B). Differentiation to chondroblasts, osteoblasts, and adipocytes was confirmed by appropriate lineage staining. By culture day 10, the ASC 2-dimensional monolayer had developed into spheroids (FIG. 8A to 8C).

Discussion

Similarities in the transplantation and regeneration of cells of the human hematopoietic system and cells of human solid tissues have been long recognized. The first allogeneic hematopoietic stem cell transplant was conducted in 1957 (Thomas E D, et al, N Engl J Med. 1957 257(11):491-496). The first transplantation events set the stage for rapid accrual of scientific research to exploit the therapeutic potential of HSCs from bone marrow and MSCs from solid tissues.

In hematopoietic cell transplantation, while several types of cells may be transplanted, HSCs are the necessary constituents (Weissman I L, et al. Blood. 2008 112(9):3543-3553). HSCs are multipotent cells that self-renew and regenerate most, if not all, of the cellular populations found in blood (Till J E, et al. Proc Natl Acad Sci USA. 1964 51:29-36; Kim H J, et al. Dev Reprod. 2017 21(1):1-10; Spangrude G J, et al. Science. 1988 241(4861):58-62). Similarly, MSCs also self-renew and are multipotent, with the ability to regenerate solid tissues such as fat, bone, cartilage, nerve, and muscle (Brown S A, et al. Plast Reconstr Surg. 2010 126(6):1936-1946; De Francesco F, et al, Tissue Eng Part B Rev. 2015 21(6):572-584; Zuk P A, et al. Tissue Eng. 2001 7(2):211-228; Zuk P A, et al. Mol Biol Cell, 2002 13(12):4279-4295). As both HSCs and MSCs reside in the bone marrow, MSCs support hematopoiesis and associated connective tissue. While bone marrow remains a reliable source of MSCs, solid mesenchymal tissues contain greater quantities of MSCs than marrow (Sakaguchi Y, et al. Arthritis Rheum. 2005 52(8):2521-2529). Accordingly, using solid donor mesenchymal tissues for MSC transplantation and regeneration may intend safety, economic, and logistic benefits.

Since their development almost four decades ago, paramagnetic microbeads (or microspheres) have shown great utility in cell separation assays (Ugelstad J, et al. Advances in colloid and interface science. 1980 13(1-2):101-140; Ugelstad J, et al. Blood Purif. 1993 11(6):349-369; Neurauter A A, et al. Adv Biochem Eng Biotechnol. 2007 106: 41-73). In 2017, the Food & Drug Administration approved the first cell therapy for leukemia which uses paramagnetic microspheres to isolate T cells. The T cells were subsequently culture expanded and reinfused. Paramagnetic microspheres, with their polymer shell covering a uniform-sized ferrous core, allow attachment of bioreactive molecules which aid in separation of selected cellular subpopulations. In the current study, primary antibody and secondary ASC-selective antibodies were bound to paramagnetic microspheres which were previously coated with protein-G affinity matrix. A rabbit anti-mouse IgG antibody was applied first. The secondary antibodies were mouse anti-human IgG antibodies of specific clusters of differentiation. These secondary antibodies, CD44, CD73, CD90, and CD105, correspond to known antibodies which attach to and define ASCs (Bourin P, et al. Cytotherapy. 2013 15(6):641-648). While the ASC-specific antibodies may be conjugated directly to the paramagnetic beads, concern for steric hindrance, theoretically reducing cell conjugation, led to this dual layering of IgG antibodies. While ASCs in suspension maintain a spherical shape with extensive undulating surface features (Raimondo S, et al. J Anat. 2006 208(1):3-12), termed pseudopodia, we theorized that maximizing separation of the antigen binding sites by the use of selected secondary antibodies would provide greater binding opportunity as well as binding strength as the PIBs situated between the pseudopodia. The greater attachment force would maximally complement the required high magnetic gradient to counteract the significant drag forces within the lipoaspirate. A corresponding neodymium bar magnet was selected for generation of a high magnetic gradient. Additionally, triturating the lipoaspirate (transferring the lipoaspirate between syringes repeatedly) to a fine heterogeneous suspension likely aided the magnetic precipitation of the aPIBs by decreasing magnetic drag (possibly by stripping some ASCs from the stroma thus increasing magnetic cellular velocity).

During this positive selection technique for antibody-mediated enrichment of ASCs, certainly other nucleated cells were isolated as part of the immunoprecipitated cellular population. However, culture expansion of this population selected an apparent single cell population phenotypically consistent with functional ASCs, as defined by morphology, colony development, and trilineage differentiation. Additionally, flow cytometry clearly displayed isolated cells exhibiting the CD90 and CD105 markers, as found on ASCs. Not unexpectedly, the PIBs themselves exhibited intense auto-fluorescence, shadowing the representative fluorescence of the APC marker for CD73 and the PE marker for CD44. Unconjugating the aPIBs will be needed to confirm the presence of these antibodies. However, leaving the aPIBs conjugated for expansion and tri-lineage differentiation did not seem to alter respective ASC function. Follow-on studies will optimize the quality and quantity of the enriched ASCs.

The technique presented in this study may isolate clinically useful quantities of ASCs without culturing, as is typically found with many therapies using BMSCs. While BMSCs certainly can be used in therapy as primary cells, in vitro expansion of BMSCs requires days to weeks to reach quantities necessary for maximal efficacy. However, as ASCs are more numerous in solid tissues, a clinically therapeutic quantity of primary ASCs may be isolated and infused at the point-of-care. Additionally, studies have highlighted other related risks and tradeoffs of in vitro expansion, to include contamination, influences on proliferating, differentiation and homing potential (Bonab M M, et al. BMC Cell Biol. 2006 7:14-2121-7-14; Chachques J C, et al. Int J Cardiol. 2004 95 559 Suppl 1:S29-33; Rombouts W J, et al. Leukemia. 2003 17(1):160-170), and acquisition of tumorigenic properties (Kim H J, et al. Dev Reprod. 2017 21(1): 1-100; Miura M, et al. Stem Cells. 565 2006 24(4):1095-1103; Tolar J, et al. Stem Cells. 2007 25(2):371-379). Such risks would be reduced by the use of primary ASCs.

CONCLUSIONS

This study validates that functional ASCs may be isolated from aspirated adipose tissue by magnetic enrichment in 20 minutes. As the aspiration of adipose tissue and the subsequent enrichment of ASCs do not require electricity, primary therapeutic ASCs may now be isolated in any point-of-care setting, even in developing countries where access to electricity is difficult if not impossible.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A paramagnetic immunobead (PIB) for isolating human adipose-tissue derived stem cells, consisting of a magnetic material displaying on its surface a first antibody that selectively binds human CD90, a second antibody that selectively binds human CD44, a third antibody that selectively binds human CD105, and a fourth antibody that selectively binds human CD73, wherein the magnetic material is a paramagnetic spherical polymer particle.

2. The PIB of claim 1, wherein a primary antibody is conjugated to the surface of the magnetic material, wherein the primary antibody selectively binds a constant region of the first antibody, second antibody, third antibody, and fourth antibody.

3. A method for isolating human adipose-tissue derived stem cells (ASCs), comprising
   (a) obtain a lipoaspirate from a human subject,
   (b) mixing the lipoaspirate with the PIBs of claim 1
   (c) applying a magnetic field to immunoprecipitate a stromal vascular fraction (SVF) from the lipoaspirate;
   (d) discarding the lipoaspirate; and
   (e) resuspending and culturing the SVF fraction under conditions suitable to expand ASCs from the SVF.

4. The method of claim 3, wherein the magnetic field is applied using a neodymium magnet.

5. The method of claim 3, wherein the ASCs are isolated without enzymatic digestion of the lipoaspirate.

\* \* \* \* \*